US006221669B1

(12) United States Patent
Livesey et al.

(10) Patent No.: US 6,221,669 B1
(45) Date of Patent: *Apr. 24, 2001

(54) PROLONGED PRESERVATION OF BLOOD PLATELETS

(75) Inventors: Stephen A. Livesey, Conroe; Jerome Connor, The Woodlands; Laura M. Currie, Spring, all of TX (US)

(73) Assignee: LifeCell Corporation, Branchburg, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/600,343

(22) Filed: Feb. 13, 1996

Related U.S. Application Data

(63) Continuation-in-part of application No. 08/326,036, filed on Oct. 19, 1994.

(51) Int. Cl.⁷ .......................... G01N 31/00; A61K 35/14
(52) U.S. Cl. .................................. 436/18; 422/1
(58) Field of Search .................... 436/18; 422/1

(56) References Cited

U.S. PATENT DOCUMENTS

| | | | |
|---|---|---|---|
| 4,665,088 | 5/1987 | Apitz-Castro et al. | 514/420 |
| 4,764,463 | 8/1988 | Mason et al. | 424/101 |
| 4,940,581 | 7/1990 | Mason et al. | 424/532 |
| 4,983,514 | 1/1991 | Weithmann et al. | 435/29 |
| 4,994,367 | 2/1991 | Bode et al. | 435/2 |
| 5,162,571 | * 11/1992 | Shiraishi et al. | |
| 5,256,559 | 10/1993 | Maraganore et al. | 435/240.2 |
| 5,622,867 | * 4/1997 | Livesey et al. | |

FOREIGN PATENT DOCUMENTS

| | | | |
|---|---|---|---|
| 0108588 | 5/1984 | (EP) | A01N/1/02 |
| 0291873 | 11/1988 | (EP) | C12Q/1/56 |
| WO90/06128 | 6/1990 | (WO) | A61K/37/02 |
| WO94/02015 | 2/1994 | (WO) | A01N/1/02 |

OTHER PUBLICATIONS

Contant et al., "Heparin Inactivation During Blood Storage: Its Prevention by Blood Collection in Citric Acid, Theophylline, Adenoisine, Dipyridamole—CTAD Mixture", Thrombosis Research, vol. 31, No. 2, pp. 365–374, Jul. 15, 1983.

Murakami et al., "Potentiating Effect of Adenosine on Other Inhibitors of Platelet Aggregation", Thrombosis et Diathesis Haemorrhagica, vol. 27, No. 2, pp. 252–262, Apr. 30, 1972.

Bode et al., "The Use of Inhibitors of Platelet Activation or Protease Activity in Platelet Concentrates Stored for Transfusion", Blood Cells, vol. 18, No. 3, pp. 361–380, 1992.

Teng et al., "Triwaglerin: a potent platelet aggregation inducer purified from *Trimeresurus wagleri* snake venom", Biochimica et Biophysica Acta. 992 (1989) pp. 258–264.

Teng et al., "Platelet Aggregation Induced by Equinatoxin", Thrombosis Research, vol. 52, 1988) pp. 401–411.

Narayanan, "Inhibition of In Vitro Platelet Aggregation and Release and Fibrinolysis", Annals of Clinical and Laboratory Science, vol. 19, No. 4, pp. 260–265, 1989.

Valari et al., "a Simple Method for Freezing Human Platelets Using 6% Dimethysolfoxide and Storage at —80° C.", Blood, vol. 43, No. 1 (Jan.), 1974 pp. 131–136.

Bode, et al., "Extended Storage of Platelets by *Fusobacterium necrophorum*", Journal of Clinical Microbiology, vol. 22, No. 2, Aug. 1985, pp. 245–249.

Canizares, et al., "Role of the microtubular system in platelet aggregation", Brazilian J Med Biol Res, (1994) 27; pp. 1533–1551.

Kuhne et al., "Flow Cytometric Evaluation of Platelet Activation in Blood Collected into ECTA vs. Diatube–H, a Sodium Citrate Solution Supplemented with Theophylline, Adenosine, and Dipyridamole", American Journal of Hematology 50:pp. 40–45 (1995).

Karrenbrock et al., "A comparative study of the effects of SIN–1, sodium nitroprusside and nitrates on inhibition of platelet aggregation and activation of soluble guanylate–cyclase in human platelets (in French)", Path Biol, 1987, 35 No. 2 bis, pp. 251–254.

Siffert et al., "Inhibition of Platelet Aggregation by Amiloride", Thrombosis Research 44, pp. 235–240, 1986.

Becker et al., "Effect of Prostaglandin E1 on Harvesting of Plates from Refrigerated Whole Blood" J. Lab. Clin. Med. (1974) 83(2), pp. 304–9 , abstract.

* cited by examiner

*Primary Examiner*—Gary L. Kunz
*Assistant Examiner*—Sharon L. Turner
(74) *Attorney, Agent, or Firm*—Howrey Simon Arnold & White, LLP

(57) ABSTRACT

This invention provides a method for prolonging the preservation of human blood platelets at reduced temperatures. The method uses an inhibitor system that enables blood platelets to retain their functional integrity during storage. In addition, the inhibitor system prevents the generation of cytokines in the platelet preparation during storage at both 22° C. and 4° C. This is accomplished by interrupting normal platelet function during storage, so as to help keep platelets from activating and losing their shape. Before using the platelets in a transfusion, they are returned to their normal functional level by washing the inhibitor system away from the platelets.

7 Claims, No Drawings

PROLONGED PRESERVATION OF BLOOD PLATELETS

This is a continuation-in-part of U.S. patent application Ser. No. 08/326,036 filed on Oct. 19, 1994.

BACKGROUND OF THE INVENTION

1. Field of the Invention

This invention relates to a method for extending the shelf-life of human blood platelets. The invention relates particularly to a reversible inhibitor system and method that inhibits platelets from biologically activating during storage at refrigeration temperatures (4° C.) but leaves platelets with the ability to resume normal reactions once the inhibitor system is removed.

2. Description of Related Art

Platelet transfusions are frequently used to treat patients. Not only are platelet transfusions given to casualty victims suffering from massive blood loss, but also to patients undergoing chemotherapy. Chemotherapy reduces the number of a patient's platelets, and also causes the platelets that are present to function defectively. For example, with thrombocytopenia, a patient has a decreased number of platelets caused by bone marrow suppression, whereas a patient with hemorrhagic myocarditis may have platelets that have been rendered functionally defective by chemotherapy. Platelet transfusions are used to increase the number of platelets to treat conditions such as thrombocytopenia, and to replace functionally defective platelets in treating hemorrhagic myocarditis.

Blood platelets should be stored at the lowest temperature possible to reduce metabolic function, contaminant growth and the generation of cytokines. Currently, platelets are stored for up to 5 days at 22° C. This storage time is limited by a decrease in pH due to increased lactate associated with anaerobic metabolic activity. Storage at 22° C. is also limited by the potential for bacterial growth. Refrigeration offers advantages over 22° C. storage with respect to metabolic function, contamination, and pH stability. However refrigerated storage results in multiple inherent problems. First, platelets undergo a change from discoid shape to a spherical configuration after about 24 hours of refrigerated storage. Second, spontaneous aggregation is increased after 24–48 hours of refrigerated storage. Third, platelets stored at 4° C. fail to recover functional activity following the storage period. Finally, platelets which undergo a storage lesion at 4° C. are cleared from the circulation by the spleen following transfusion.

Goals for refrigerated platelet storage are to preserve a high number of platelets, lengthen the time that platelets may be preserved, maintain the functional integrity of platelets, inhibit the production of cytokines in the platelet preparation, and ensure that their in vivo circulatory life span approaches normal limits. This may be accomplished by using the inhibitor system of this invention, because it blocks pathways that are essential to activation, thus rendering the platelet unsusceptible to 4° C. induced damage.

Since fresh platelets have a shelf-life of only 3 to 5 days at 22° C. (room temperature), methods for extending platelet shelf-life would be beneficial. Unfortunately, despite a number of attempts to optimize platelet storage, progressive changes in cell shape (resulting in biological disfunction) and permanent deterioration in subsequent aggregation potential continue to limit platelet storage. Cytokines generated during the storage of platelet concentrates can cause febrile reactions in recipient patients. In addition, platelets develop a lesion with storage that causes them to be removed from the circulation, predominantly by the spleen during the first passage following transfusion. In addition, For instance, the typical life span of a normal platelet in the human body is approximately eight days. Prior art attempts to store platelets for extended periods of time result in the creation of lesion-modified platelets. Approximately 80%–90% of the prior art storage platelets can be numerically recovered after storage, but only 20%–35% remain active after the first circulatory flow through the spleen. This is because the spleen filters out the lesion-modified platelets. Use of the compositions and methods of this invention result in the same 80%–90% numerically recovered as the prior art, but since lesion-modified platelets are not produced, 65% to 80% of the reactivated platelets should function biologically for the typical time in the human body.

Several approaches such as reduced storage temperature, cryopreservation techniques, additives and artificial storage media yield an increased number of platelets following storage. However, the functional capacity and persistence in circulation of the platelets recovered by these methods is limited. Blood banks and hospitals very much need a platelet storage system that provides an increased number of platelets after storage, but also prevents platelets from aggregating during storage and enables them to continue to retain the ability to react normally once they are transfused into a patient including the ability of platelets to persist in the circulation and not be cleared.

Blood banks and hospitals very much need a platelet storage system that will provide an increased number of platelets after storage. This may be accomplished by a platelet storage system that: prevents platelets from aggregating during storage; prevents the production of a febrile reaction in patients produced by cytokines; enables platelets to regain the ability to react normally after removal from storage; and allows platelets to persist in circulation and avoid being cleared by the spleen.

Previous attempts to use platelet activation inhibitors have met with very limited success. This is primarily because the prior art teaching is limited to the use of a single inhibitor in an attempt to preserve platelet function. The single inhibitor system results in improved results over no inhibitor at all but does not approach the unexpected results achieved using the compositions and methods of the subject invention. Prior methods for the use of single inhibitor systems are explained in Valeri, Feingold, and Marchionni, *A Simple Method for Freezing Human Platelets Using Dimethylsulfoxide and Storage at −80° C., Blood,* Vol. 43, No. 1 (January), 1974 and Bode, Holme, Heaton, and Swanson, *Extended Storage of Platelets in an Artificial Medium with the Platelet Activation Inhibitors Prostaglandin E, and Theophylline,* Vox Sang 1991:60;105–112.

The instant invention represents a quantum leap in beneficial result and technical sophistication over the prior methods. The platelet storage, reactivation, and long term functional effectiveness of blood platelets treated with the compositions and methods of this invention have previously been considered impossible.

SUMMARY OF THE INVENTION

This invention provides a method for prolonging the preservation of human blood platelets. The method uses an inhibitor system that enables blood platelets retain their functional integrity during prolonged storage. This is accomplished by inhibiting normal platelet function, so as to help keep platelets from biologically activating during storage.

The method of this invention broadly comprises an inhibitor system that is made up of second messenger effectors. This second messenger inhibitor system functions through the following pathways: cyclic adenosine monophosphate (cyclic AMP), sodium channel, cyclic guanosine monophosphate (cyclic GMP), cyclooxygenase, lipoxygenase, phospholipase, the calcium cascade, protease and proteinase, and membrane modification. More specifically, special agents or combinations of agents may be used for each of the pathways. For example, adenosine, iloprost, prostacyclin and $PGE_2$ act to inhibit activation through stimulation of the cyclic AMP pathway. Amiloride and amiloride analogues act to inhibit activation through inhibition of the sodium channel. Sodium nitroprusside and L-arginine act to inhibit activation through stimulation of the cyclic GMP pathway. Aspirin, dipyridamole, flurbiprofen, and ticlopidine act to inhibit activation through inhibition of the cyclooxygenase pathway. Aspirin and ticlopidine act to inhibit platelet activation through inhibition of the lipoxygenase pathway. Quinacrine acts to inhibit platelet activation through the inhibition of the phospholipase pathway. Calcium acts to promote platelet activation through the calcium cascade. Protease and or proteinases act to inhibit platelet aggregation through the inhibition of surface receptor changes. Amantadine, ajoene, heparin, ticlopidine, and/or pentoxifylline act as membrane modifiers. The inhibitor systems described function during storage at low temperatures, i.e. from 2 to 8° C.

A preferred method for human platelet preservation begins by drawing whole human blood via venipuncture into a blood bag storage system containing an anticoagulant. The blood is centrifuged to isolate platelet-rich plasma from the blood. The platelet-rich plasma is centrifuged to separate platelet-poor plasma from the platelet pellet, which is the concentrated platelets left after centrifuging and decanting the plasma. Approximately one-fourth of the plasma is left on the platelet pellet. Next, an inhibitor system is added to the platelet pellet. This inhibitor system is comprised of solutions of the following substances that are added to the platelets and result in the following concentrations: from 0.1 mM to 10 mM, preferably about 0.25 mM amiloride in phosphate buffered saline; from about 2.5 uM to about 250 uM, preferably about 50 uM sodium nitroprusside (NaNP) in phosphate buffered saline; from about 10 uM to about 1 mM, preferably about 0.1 mM adenosine in phosphate buffered saline; from about 10 nM to about 1 uM, preferably about 0.2 uM quinacrine in phosphate buffered saline; from about 2 uM to about 200 uM, preferably 40 uM dipyridamole in phosphate buffered saline; from about 0.5 mM to about 5 mM, preferably 0.75 mM ticlopidine in phosphate buffered saline. The platelet pellet is gently resuspended in the inhibitor system mixture. The mixture is then placed in a platelet storage container and stored at (2°–8° C.) without agitation.

DETAILED DESCRIPTION OF THE PREFERRED EMBODIMENTS

Activation during storage is undesirable. However, platelets must retain the ability to activate when they are taken out of storage to function normally for transfusion purposes. When the platelets are removed from storage, the inhibitor system of this invention may be washed from the platelets, which allows them to return very closely to their normal level of activity. This washing step can be achieved in vitro by mechanical washing or by a dilution effect from direct transfusion.

There are three platelet activity parameters that are measured to determine whether platelets have retained their functional ability after storage. These parameters are useful when they are compared to the same parameters for fresh platelets. Additionally, the platelet activity parameters for platelets stored with different inhibitor mixtures may be compared to determine which inhibitor combinations yield more functional platelets after storage. The tests used to measure platelet activity parameters preserved by this invention are: platelet number, hypotonic stress response, collagen-induced aggregation and adenosine diphosphate (ADP)-induced aggregation.

Hypotonic stress response is an assay used to determine if platelets have retained metabolic viability. This assay is a photometric measurement of the platelets' ability to overcome the addition of a hypotonic solution. This activity reflects cell function (i.e. a functional membrane water pump) and is indicative of platelet recovery following storage. Hypotonic stress response has been demonstrated to be an important indicator of platelets' ability to survive in circulation following transfusion. Consequently, hypotonic stress response represents a crucial parameter for evaluating platelet biochemistry following storage.

Potential for aggregation is another feature that demonstrates whether blood platelets have maintained their functional integrity during storage. This potential is measured by using ADP and collagen to induce aggregation. An agonist is an agent that binds to a receptor and initiates a certain response. In an agonist-induced aggregation, the aggregation or clumping is the response. The agonists, ADP and collagen, are used to induce aggregation to determine if platelets have retained their ability to aggregate. In addition, when performing aggregation responses one can detect the presence of spontaneous aggregation, that is the platelets adhering to each other without the addition of an agonist. The occurrence of spontaneous aggregation has been correlated with removal of platelets from the circulation and hence have short survival times.

The presence of cytokines in platelet concentrates, following storage at 22° C., has been associated with febrile reactions in patients following transfusions. The source of these cytokines specifically, IL6, IL-1β and TNF, are the white blood cells which are present in the stored platelet preparations. The amount of these cytokines produced in a platelet concentrate during storage can be determined by use of an enzyme linked immuno-specific assay (ELISA) kit which quantifies the amount of each cytokine.

A. The Inhibitor System

The inhibitor system of this invention is based on the application of specific second messenger effectors, which interact with the platelets and stabilize the cells to resist loss of viability and functional activity and prevent the production of cytokines during storage at 4° C.

The Six Component Mixture

Specific modifiers that make up the preferred six component inhibitor system are amiloride, adenosine, sodium nitroprusside, quinacrine, dipyridamole, and ticlopidine. These modifiers are added to the platelet pellet from a 50-fold concentrate suspended in phosphate-buffered saline. Each of these modifiers affects a different specific second messenger pathway. Amiloride is a potassium conserving diuretic, employed medicinally in the treatment of hypertension. In this invention, amiloride acts as an inhibitor of the platelet $Na^+$—$H^+$ exchanger. Adenosine is used medicinally to restore normal sinus rhythm in patients. In this invention, adenosine stimulates the production of cyclic AMP. Sodium nitroprusside relaxes smooth muscle thus serving as a vasodilator, medicinally. In this invention, sodium nitroprusside stimulates the production of cyclic GMP. Dipyridamole is employed medicinally as a platelet adhesion inhibitor. In this invention, dipyridamole acts as an inhibitor of cyclooxygenase and lipoxygenase enzymes of the arachidonic acid cascade. Quinacrine is used in the treatment to eradicate intestinal cestodes. In this invention, quinacrine serves as a phospholipase $A_2$ inhibitor. Medicinally, ticlopidine is used as a platelet aggregation inhibitor to reduce the risk of thrombotic strokes. In this invention, ticlopidine is used as an inhibitor of the arachidonic acid cascade.

All of the second messenger effectors have been demonstrated to inhibit agonist induced aggregation both separately and in combination with the others. More importantly, the inhibition is reversible following removal of the effector(s) by washing the platelets. Upon adding the second messenger effectors, both individually or in combination, platelets were less susceptible to storage lesions during storage at 2 to 8° C. These cells also displayed normal aggregation physiology upon removal of the effector(s), they also did not display spontaneous aggregation and maintained a high hypotonic stress response. The storage of platelets with the second messenger effectors prevented the production of the cytokines IL6, IL1-β and TNF, both at 4° C., and in platelet preparation stored according to standard methods at 22° C.

In describing the chemicals which have shown utility as platelet lesion inhibitors and cytokine production inhibitors, it must be understood that the actual chemicals mentioned together with functionally equivalent materials are intended to be within the scope of this invention. Chemicals that are known to applicants to have known or demonstrated utility as inhibitors have been specifically set forth in the instant application. However, it is intended that the scope of the application be extended to other functionally effective chemicals, both existing chemicals and chemicals yet to be discovered.

Certain chemicals which are thought to be functionally equivalent materials for the inhibitor acting through the sodium channel are those selected from the group consisting of amiloride, amiloride analogues, bepridil, flecainide, saxitoxin, benzamil and prajnalium. Materials thought to be functionally equivalent to the inhibitor acting through the GMP pathway are selected from the group consisting of sodium nitroprusside, L-arginine, nitrous oxide, SIN-1, SIN-1A, atrial natriuretic factor, vasopressin, oxytocin, and glyceryl trinitrate. Functionally equivalent materials for the inhibitor acting through the cyclooxygenase pathway are selected from the group consisting of aspirin, dipyridamole, flurbiprofen, and ticlopidine, ketoprofen, ibuprofen, indomethacin, sulfinpyrazone, guanabenz, ursolic acid and benzohydroquinone. Functionally equivalent materials for the inhibitor component acting through the lipoxygenase pathway are selected from the group consisting of aspirin, ticlopidine, ursolic acid, unbelliferone, 5,8,11,14 eicosatetraynoic acid and esculetin. Finally, functionally equivalent materials to the inhibitor acting through the calcium cascade are selected from the group consisting of protein kinase C effectors, calcium channel blockers, calcium concentration modifiers, calmodulin effectors, calcium ionophores and ATPase stimulators.

B. Storing Platelets at 4° C.

The shelf-life of blood platelets may be successfully extended by storing the cells at 4° C. with the inhibitor system of this invention. When platelets that were stored at 4° C. for 10 days were analyzed for post-storage activity, as compared to the activity of fresh platelets, the percentage of the cells' activity was as follows: 70% ADP-induced aggregation, 85% collagen-induced aggregation, 65% hypotonic stress response and >95% recovery of cell number. These results compare favorably to conventional storage of platelets at 22° C. following 5 days of storage which yielded 55% ADP-induced aggregation, 80% collagen-induced aggregation and 50% hypotonic stress response, as compared to fresh platelets.

To perform the 4° C. experiment, whole blood is drawn via venipuncture into blood bags containing the anti-coagulant acid-citrate dextrose as prescribed by the procedures and protocols of the American Association of Blood Banks and performed by a blood procurement agency. The blood bags are centrifuged at 2000×g for 3 minutes to separate the red blood cells from the platelets and the plasma The platelet-rich plasma is isolated by expression into a connected platelet storage bag followed by a second centrifugation at 5000×g for 5 minutes to pellet the platelets. The platelet-poor plasma is expressed into a plasma storage bag, while the resulting platelet pellet, with approximately 50–60 milliliters of plasma is left for one hour at 22° C. as prescribed by blood banking procedures. Following the incubation, the platelet preparation is resuspended in the residual plasma by gentle shaking.

An inhibitor system solution is prepared as follows: A solution of reagents is prepared in phosphate buffered saline containing 12.5 mM amiloride, 37.5 mM ticlopidine, and 2 mM dipyridamole, 2.5 mM sodium nitroprusside, 5 mM adenosine, 10 uM quinacrine. The concentration of the inhibitor system reagents in these mixtures is 50-fold the final concentration needed in the platelet preparation to achieve effective storage at 4° C. The inhibitor solutions are added to the platelet concentrate at a ⅟₅₀ volume of the total platelet preparation volume via a direct injection through a sterile port. The final concentration of the inhibitor reagents in the platelet preparation is as follow: amiloride—0.25 mM, adenosine—0.1 mM, sodium nitroprusside—50 uM, dipyridamole—40 uM, quinacrine—0.2 uM, and ticlopidine—0.75 mM. The platelet preparation in a standard platelet storage bag is placed at 4° C. without agitation. The platelet concentration with the inhibitor system can be directly transfused following storage.

The following examples are provided to enable those of ordinary skill in the art to make the compositions of this invention. These examples are not intended to limit the scope of what the inventors regard as their invention. Efforts have been made to ensure accuracy with respect to numbers used to characterize the measured conditions; however, some experimental errors and deviations may be present.

EXAMPLE 1

The following describes an example of the application of the inhibitor system of this invention to the storage of a whole unit platelet concentrate for extended period at 4° C. A whole unit of whole blood was drawn via venipuncture at the Gulf Coast Regional Blood Bank according to standard blood banking techniques into a sterile commercial blood collection system. The blood bag containing the whole blood was centrifuged according to standard blood banking procedures and the resultant platelet-rich plasma fraction was expressed into a standard platelet storage bag. The platelet-rich plasma was then centrifuged according to the blood banking protocol and the resultant platelet-poor plasma was expressed into a standard plasma storage bag. The resultant platelet pellet in the platelet storage bag still retains approximately 60 milliliters of plasma. This platelet concentrate is stored without agitation for one hour at 22° C. to allow the platelets to resuspend. A solution of inhibitors is prepared which contains the following: A solution of reagents is prepared in phosphate buffered saline containing 12.5 mM amiloride, 37.5 mM ticlopidine, and 2 mM dipyridamole, 2.5 mM sodium nitroprusside, 5 mM adenosine and 10 uM quinacrine. The concentration of the inhibitor system reagents in these mixtures is 50 fold the final concentration needed in the platelet preparation. The inhibitor solutions are added to the platelet concentrate at a 1/50 volume of the total platelet preparation volume (approximately 1.2 milliliters) via a direct injection through a sterile port. The final concentration of the inhibitor reagents in the platelet preparation is as follows: amiloride—0.25 mM, adenosine—0.1 mM, sodium nitroprusside—50 uM, dipyridamole—40 uM, quinacrine—0.2 uM, and ticlopidine—0.75 mM. The platelet concentrate with the inhibitor solution is then stored at 4° C., without agitation. In parallel, as a means of comparison, a platelet concentrate unit was stored under the current blood banking method as follows: after the one hour incubation of the platelet concentrate to allow resuspension, the platelet preparation was stored at 22° C., with and without the second messenger effectors, with gentle agitation following standard blood banking procedures. In addition, a platelet concentrate preparation was stored at 4° C. without the inclusion of the inhibitor system. At various time intervals of storage, an aliquot of platelets was harvested from the conventionally stored preparation with and without the inhibitor treatment, the platelets stored at 4° C., and the platelets stored at 4° C. with the inclusion of the inhibitor solution of this invention. Platelets from these preparations were then analyzed for viability and functional activity of the cells and for the presence of the cytokines IL6, IL-Iβ and TNF. The results of this experiment are shown in the following tables. The data is expressed as a percentage of the viability and functional activity of fresh platelets at the time of acquisition.

| | % of Fresh Platelets | | | | | |
|---|---|---|---|---|---|---|
| | ADP-Induced Aggregation | | Collagen-Induced Aggregation | | Hypotonic Stress Response | |
| Time (days) | 5 | 10 | 5 | 10 | 5 | 10 |
| 22° C. Storage | 32 | 28 | 67 | 42 | 35 | 57 |
| 4° C. Storage | 23 | 15 | 44 | 31 | 34 | 22 |
| Inhibitor System Storage | 54 | 58 | 89 | 83 | 86 | 65 |

In all tests of viability and functional activity, the platelet concentrate stored at 4° C. with the addition of the inhibitor system of this invention displayed higher recovery at day 10 than the conventionally stored platelets at day 5. Under current blood bank practices the maximum storage time for platelets is 5 days at 22° C. The concentration of the cytokines IL6, IL-1β and TNF were determined for the above stored platelet concentrate over the 10 day storage period.

| Cytokine Production in Stored Platelet Concentrates (pg/ml) | | | | | | | | | |
|---|---|---|---|---|---|---|---|---|---|
| | Treated Platelets Stored at 4° C. | | | Treated Platelets Stored at 22° C. | | | Control Platelets Stored at 22° C. | | |
| | Day 1 | Day 5 | Day 10 | Day 1 | Day 5 | Day 10 | Day 1 | Day 5 | Day 10 |
| IL6 | 3.0 | 2.4 | 2.5 | 2.7 | 50.2 | 53.1 | 3.1 | 229.5 | 257.3 |
| IL-Iβ | 0.57 | 0.58 | 0.90 | 4.2 | 13.0 | 20.1 | 2.4 | 86.2 | 137.8 |
| TNF | 5.4 | 7.6 | 5.0 | | | | 8.7 | 43.1 | 46.4 |

For all of the cytokine tested the inhibitor-treated platelet preparations produced lower amounts of cytokines during storage regardless of the incubation temperature of the cells.

What is claimed is:

1. A platelet storage composition comprising, a plasma excipient for platelet storage comprising between about 0.1 mM and 10 mM amiloride, between about 2.5 $\mu$M and 250 $\mu$M sodium nitroprusside, between about 10 $\mu$M and 1 mM adenosine, between about 10 nM and 1 $\mu$M quinacrine, between about 2 $\mu$M and 200 $\mu$M dipyridamole; and between about 0.5 mM and 5 mM ticlopidine, said platelet storage composition enabling the storage of bioactive platelets for 10 days.

2. The composition of claim 1 wherein said amiloride concentration is about 0.25 mM amiloride.

3. The composition of claim 1 wherein said sodium nitroprusside concentration is about 50 uM.

4. The composition of claim 1 wherein said adenosine concentration is about 0.1 mM.

5. The composition of claim 1 wherein said quinacrine concentration is about 0.2 uM.

6. The composition of claim 1 wherein said dipyridamole concentration is about 40 uM.

7. The composition of claim 1 wherein said ticlopidine concentration is about 0.75 mM.

* * * * *